US008273951B2

(12) United States Patent
McGonigle

(10) Patent No.: US 8,273,951 B2

(45) Date of Patent: Sep. 25, 2012

(54) DOWN-REGULATION OF GENE EXPRESSION USING ARTIFICIAL MICRORNAS

(75) Inventor: Brian McGonigle, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/348,215

(22) Filed: Jan. 11, 2012

(65) Prior Publication Data

US 2012/0107939 A1 May 3, 2012

Related U.S. Application Data

(62) Division of application No. 12/335,704, filed on Dec. 16, 2008, now Pat. No. 8,115,055.

(60) Provisional application No. 61/014,510, filed on Dec. 18, 2007.

(51) Int. Cl.
*C12N 15/09* (2006.01)
*C12N 15/82* (2006.01)
*A01H 5/00* (2006.01)

(52) U.S. Cl. ........ 800/285; 800/278; 800/298; 800/320; 435/468; 435/320.1; 435/419; 536/23.1

(58) Field of Classification Search ........................ None
See application file for complete search history.

(56) References Cited

U.S. PATENT DOCUMENTS

| | | | |
|---|---|---|---|
| 8,030,473 B2 | 10/2011 | Carrington et al. | |
| 2005/0075492 A1 | 4/2005 | Chen et al. | |
| 2005/0120415 A1 | 6/2005 | Aukerman | |
| 2005/0138689 A1 | 6/2005 | Aukerman | |
| 2005/0144669 A1 | 6/2005 | Reinhart et al. | |

FOREIGN PATENT DOCUMENTS

| | | |
|---|---|---|
| WO | WO 2004009779 | 1/2004 |
| WO | WO 2006044322 B1 | 4/2006 |

OTHER PUBLICATIONS

Allshire, Science, RNAi and Heterochromatin—a Hushed-Up Affair, vol. 297, pp. 1818-1819, 2002.
Alvarez et al., Plant Cell, Endogenous and Synthetic MicroRNA's Stimulate Simultaneous, Efficient and Localized Regulation of Multiple Targets in Diverse Species. vol. 18, pp. 1134-1151, 2006.
Bartel, Cell, MicroRNA's: Genomics, Biogenesis, Mechanism and Function. vol. 116, pp. 281-297, 2004.
Cuperus, et al., "Unique Functionality of 22-nt miRNAs In Triggering RDR6-dependent . . . ", Nature Structural & Molecular Biology, vol. 17 (8), pp. 997-1004, Aug. 2010.
Elbashir et al., Genes & Development, RNA Interference is Mediated by 21- and 22-nucleotide RNAs, vol. 15, pp. 188, 2001.
Elbashir et al., Nature, Duplexes of 21-Nucleotide RNAs Mediate RNA Interference in Cultured Mammalian Cells, vol. 411, pp. 494, 2001.
Fire et al., Nature, Potent and Specific Genetic Interference by Double-Stranded RNA in *Caenorhabditis elegans*, vol. 391, pp. 806, 1998.
Grishok et al., Cell, Genes and Mechanisms Related to RNA Interference Regulate Expression of the Small Temporal RNAs that Control *C. elegans* Developmental Timing, vol. 106, pp. 23-34, 2001.
Hall et al., Science, Establishment and Maintenance of a Heterochromatin Domain, vol. 297, pp. 2232-2237, 2002.
Hammond et al., Nature, An RNA-Directed Nuclease Mediates Post-Transcriptional Gene Silencing in Drosophila Cells, vol. 404, p. 293, 2000.
Hutvagner et al, Science, A Cellular Function for the RNA-Interference Enzyme Dicer in the Maturation of the let-7 small Temporal RNA, vol. 293, pp. 834-838, 2001.
Hutvagner et al., Science, A microRNA in a Multiple-Turnover RNAi Enzyme Complex, vol. 297, pp. 2056-2060, 2002.
Palatnik et al., Sequence and expression differences underlie functional specialization of *Arabidopsis* MicroRNAs miR159 miR319, Developmental Cell, Jul. 2007, pp. 115-125, vol. 13, No. 1.
Jenuwein, Science, An RNA—Guided Pathway for the Epigenome, vol. 297, pp. 2215-2218, 2002.
Jones-Rhoades et al., Annual Review of Plant Biology. MicroRNA's and their Regulatory Roles in Plants, vol. 57, pp. 19-15, 2006.
Ketting et al., Genes & Development, Dicer Functions in RNA Interference and in Synthesis of Small RNA Involved in Developmental Timing in *C. elegans*, vol. 15, pp. 2654-2659, 2001.
H. Kim ET et al., Database EMBL Accession No. DR963981, ZM_BFb0083D07.4ZM_BFb *Zea mays* cDNA5', mRNA sequence, Aug. 4, 2005.
Kurihara et al., Proc Natl Acad Sci., *Arabidopsis* Micro-RNA Biogenesis through Dicer-like 1 protein function. vol. 101, pp. 12753-12758, 2004.
Lagos-Quintana et al., Science, Identification of Novel Genes Coding for Small Expressed RNAs, vol. 294, pp. 853-858, 2001.
Lagos-Quintana et al., Current Biology, Identification of Tissue-Specific MicroRNA's from Mouse. vol. 12, pp. 735-739, 2002.
Lau et al., Science. An Abundant Class of Tiny RNAs with Probable Regulatory Roles in *Caenorhabditis Elegans*, vol. 294, pp. 858-862, 2001.
Lee et al., Cell, The *C. elegans* Heterochronic Gene lin-4 Encodes Small RNAs with Antisense Complementarity to lin-14, vol. 75, pp. 843-854, 1993.
Lee et al., Science, An Extensive Class of Small RNAs in *Caenorhabditis elegans*, vol. 294, pp. 862-864, 2001.
Lee et al., The EMBO Journal, MicroRNA Maturation: Stepwise Processing and Subcellular Localization, vol. 21, pp. 4663-4670, 2002.
Llave et al., Plant Cell, Endogenous and Silencing-Associated Small RNAs in Plants, vol. 14, pp. 1605-1619, 2002.
Mallory et al., Nature Genetics, Functions of microRNA's and related small RNA's in plants, vol. 38, pp. 531-536, 2006.
Mourelatos et al., Genes & Development. miRNPs: A Novel Class of Ribonucleoproteins Containing Numerous microRNAs, vol. 16, pp. 720-728, 2002.
Niu et al., Nature Biotechnology, Expression of artificial microRNA in transgenic *Arabidopsis thaliana* confers virus resistance. vol. 24, pp. 1420-1428, 2006.
Olsen et al., Developmental Biology, the lin-4 Regulatory RNA Controls Developmental Timing in *Caenorhabditis elegans* by Blocking LIN-14 Protein Synthesis after the Initiation of Translation, vol. 216, pp. 671-680, 1999.
Obernosterer et al., RNA, Post-Transcriptional Regulation of microRNA Expression, vol. 12, pp. 1161-1167, 2007.

(Continued)

*Primary Examiner* — Medina A Ibrahim

(57) ABSTRACT

Isolated nucleic acid fragments comprising precursor miRNA, and artificial miRNAs and their use in down-regulating gene expression are described.

7 Claims, No Drawings

OTHER PUBLICATIONS

Park et al., Current Biology, Carpel Factory, a Dicer Homolog, and HEN1, a Novel Protein, Act in microRNA Metabolis in *Arabidopsis thaliana*, vol. 12, pp. 1484-1495, 2002.

J.F. Parizotto et al., Genes & Development, In vivo investigation of the transcription, processing, endonucleolytic activity, and functional relevance of the spacial distribution of a plant miRNA. vol. 18, pp. 2237-2242, 2007.

Reinhart, et al., "MicroRNAs In Plants", Genes & Development, vol. 16, pp. 1616-1626, 2002.

Reinhart et al., Nature, The 21-Nucleotide let-7 RNA Regulates Developmental Timing in *Caenorhabditis elegans*, vol. 403, pp. 901-906, 2000.

Rhoades et al., Cell, Prediction of Plant MicroRNA Targets, vol. 110, pp. 513-520, 2002.

Schwab et al., Developmental Cell, Specific Effects of MicroRNAs on the Plant Transcriptome, vol. 8, pp. 517-527, 2005.

Schwab et al., Plant Cell, Highly Specific Gene Silencing by Artificial microRNA's in *Arabidopsis*. vol. 18, pp. 1121-1133, 2006.

Schwarz et al., Cell, Asymmetry in the Assembly of the RNAi Enzyme Complex, vol. 115, pp. 199-208, 2003.

Volpe et al., Science, Regulation of Heterochromatic Silencing and Histone H3 Lysine-9 Methylation by RNAi, vol. 297, pp. 1833-1837, 2002.

Wightman et al., Cell, Posttranscriptional Regulation of the Heterochronic—Gene lin-14 by lin-4 Mediates Temporal Pattern Formation in *C. elegans*, vol. 75, pp. 855-862, 1993.

Wianny et al., Nature Cell Biol., Specific Interference with Gene Function by Double-Stranded RNA in Early Mouse Development, vol. 2, pp. 70, 1999.

M. R. Wilmann et al., Conservation and evolution of miRNA regulatory programs in plant development, Current Opinion in Plant Biology, Quadrant Subscription Services, GB, Oct. 4, 2007, pp. 503-511, vol. 10, No. 5.

Zhang et al., FEBS Letter, Identification of 188 Concerved Maize microRNAs and their Targets, vol. 580, pp. 3753-3762, 2006.

DOWN-REGULATION OF GENE EXPRESSION USING ARTIFICIAL MICRORNAS

This application claims the benefit of U.S. Provisional Application No. 61/014,510, filed Dec. 18, 2007 the disclosure of which is hereby incorporated by reference in its entirety.

FIELD OF THE INVENTION

The field of the present invention relates, generally, to plant molecular biology. In particular, it relates to constructs and methods to down-regulate expression of targeted sequences.

BACKGROUND

MicroRNAs (miRNAs) were first identified only a few years ago, but already it is clear that they play an important role in regulating gene activity. These 20-22 nucleotide non-coding RNAs have the ability to hybridize via base-pairing with specific target mRNAs and downregulate the expression of these transcripts, by mediating either RNA cleavage or translational repression.

Recent studies have indicated that miRNAs have important functions during development. In plants, they have been shown to control a variety of developmental processes including flowering time, leaf morphology, organ polarity, floral morphology, and root development (reviewed by Mallory and Vaucheret (2006) *Nat Genet* 38: S31-36). Given the established regulatory role of miRNAs, it is likely that they are also involved in the control of some of the major crop traits such drought tolerance and disease resistance.

miRNAs are transcribed by RNA polymerase II as polyadenylated and capped messages known as pri-miRNAs. These pri-miRNAs are processed into smaller transcripts known as pre-miRNAs and these precursors have the ability to form stable hairpin structures (reviewed by Bartel (2004) *Cell* 116: 281-297; Jones-Rhoades M W, Bartel D P, Bartel B. MicroRNAS and their regulatory roles in plants. Annu Rev Plant Biol. 2006; 57:19-53.) While pri-miRNAs are processed to pre-miRNAs by Drosha in the nucleus and Dicer cleaves pre-miRNAs in the cytoplasm in metazoans, miRNA maturation in plants differs from the pathway in animals because plants lack a Drosha homolog. Instead, the RNase III enzyme DICER-LIKE 1 (DCL1), which is homologous to animal Dicer, may possess Drosha function in addition to its known function in hairpin processing (Kurihara and Watanabe (2004) *Proc Natl Acad Sci* 101: 12753-12758).

Artificial microRNAs (amiRNAs) have recently been described in *Arabidopsis* targeting viral mRNA sequences (Niu et al. (2006) *Nature Biotechnology* 24:1420-1428) or endogenous genes (Schwab et al. (2006) *Plant Cell* 18:1121-1133). The amiRNA construct can be expressed under different promoters in order to change the spatial pattern of silencing (Schwab et al. (2006) *Plant Cell* 18:1121-1133). Artificial miRNAs replace the microRNA and its complementary star sequence in a precursor miRNA and substitute sequences that target an mRNA to be silenced. Silencing by endogenous miRNAs can be found in a variety of spatial, temporal, and developmental expression patterns (Parizotto et al. (2007) Genes Dev 18:2237-2242; Alvarez et al. (2006) *Plant Cell* 18:1134-51). Artificial miRNA can be constructed to both capture and extend the diversity and specificity in the patterns of silencing. To date there have been no reports of using amiRNAs in crop plants.

WO 2004/009779 published Jan. 29, 2004 describes compositions and methods for modulating gene expression in plants.

Applicant's Assignee's US Patent Application Publication 2005/0138689 published on Jun. 23, 2005 describes miRNAs and their use in silencing a target sequence.

BRIEF DESCRIPTION OF THE SEQUENCE LISTING

The invention can be more fully understood from the following detailed description and the accompanying Sequence Listing, which form a part of this application.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

SEQ ID NOs:1-10 correspond to primers useful for amplifying maize genomic microRNA (miRNA) precursors.

SEQ ID NOs:11-15 correspond to maize miRNA precursor sequences for 159c, 164h, 168a, 169r, and 396h, respectively.

SEQ ID NO:16 corresponds to the artificial miRNA (amiRNA) sequence used to silence the maize phytoene desaturase (PDS) transcript.

SEQ ID NOs:17-21 correspond to "star sequences" contained within amiRNA precursors for 159c-PDS, 164h-PDS, 168a-PDS, 169r-PDS, and 396h-PDS, respectively. Star sequences are largely the complementary sequences within the miRNA precursor that form a duplex with the miRNA.

SEQ ID NOs:22-26 correspond to amiRNA precursors for 159c-PDS, 164h-PDS, 168a-PDS, 169r-PDS, and 396h-PDS, respectively. These precursors, when expressed in maize, direct the silencing of the endogenous PDS transcript.

SEQ ID NOs:27-30 correspond to truncated amiRNA precursors 169r-PDS-sht, 169r-PDS-med, 396h-PDS-sht, and 396-PDS-med, respectively. The 169r-PDS precursor (SEQ ID NO:25) was shortened to 11% of its length (169r-PDS-sht, SEQ ID NO:27) and 35% of its length (169r-PDS-med, SEQ ID NO:28) as compared to 169r-PDS. The 396h-PDS precursor (SEQ ID NO:26) was shortened to 18% of its length (396h-PDS-sht, SEQ ID NO:29) and 46% of its length (396h-PDS-med, SEQ ID NO:30) as compared to 396h-PDS. All of the truncated precursors contained the miRNA and star sequences.

SEQ ID NOs:31-34 correspond to amiRNA precursors for 159c-FAD, 168a-FAD, 169r-FAD, and 396h-FAD, respectively. These precursors, when expressed in maize, direct the silencing of the endogenous fad2-1 (fatty acid desaturase responsible for converting oleic acid to linoleic acid) transcript.

SEQ ID NOs:35-38 correspond to miRNA-target and star sequences for lethal leaf spot.

SEQ ID NOs:39-41 correspond to miRNA-target and star sequences for multidrug resistant protein which is a transporter protein.

SEQ ID NOs:42-43 correspond to amiRNA precursor sequences for 168a-MRP and 396h-MRP, respectively. These precursors, when expressed in maize, direct the silencing of MRP which results in reduced levels of phytic acid.

SUMMARY OF THE INVENTION

The present invention concerns an isolated nucleic acid fragment comprising a precursor miRNA said precursor miRNA corresponding substantially to the deoxyribonucleotide sequence set forth in SEQ ID NO:11 (i) wherein nucleotides 430 to 450 of SEQ ID NO:11 are replaced by a first variable nucleotide subsequence ranging in size from about 19 to about 30 nucleotides depending upon the target sequence whose expression is to be reduced and (ii) further wherein nucleotides 244 to 264 of SEQ ID NO:11 are replaced by a second variable nucleotide subsequence ranging in size from about 19 to about 30 nucleotides, said second variable nucleotide subsequence being capable of hybridizing to the first variable subsequence of the precursor miRNA.

Other isolated nucleic fragments which are also of interest include the following:

a) an isolated nucleic acid fragment comprising a precursor miRNA said precursor miRNA corresponding substantially to the deoxyribonucleotide sequence set forth in SEQ ID NO:12 (i) wherein nucleotides 94 to 114 SEQ ID NO:12 are replaced by a first variable nucleotide subsequence ranging in size from about 19 to about 30 nucleotides depending upon the target sequence whose expression is to be reduced and (ii) further wherein nucleotides 163 to 183 of SEQ ID NO:12 are replaced by a second variable nucleotide subsequence ranging in size from about 19 to about 30 nucleotides, said second variable nucleotide subsequence being capable of hybridizing to the first variable subsequence of the precursor miRNA;

b) an isolated nucleic acid fragment comprising a precursor miRNA said precursor miRNA corresponding substantially to the deoxyribonucleotide sequence set forth in SEQ ID NO:13 (i) wherein nucleotides 53 to 73 of SEQ ID NO:13 are replaced by a first variable nucleotide subsequence ranging in size from about 19 to about 30 nucleotides depending upon the target sequence whose expression is to be reduced and (ii) further wherein nucleotides 97 to 117 of SEQ ID NO:13 are replaced by a second variable nucleotide subsequence ranging in size from about 19 to about 30 nucleotides, said second variable nucleotide subsequence being capable of hybridizing to the first variable subsequence of the precursor miRNA;

c) an isolated nucleic acid fragment comprising a precursor miRNA said precursor miRNA corresponding substantially to the deoxyribonucleotide sequence set forth in SEQ ID NO:14 (i) wherein nucleotides 110 to 130 of SEQ ID NO:14 are replaced by a first variable nucleotide subsequence ranging in size from about 19 to about 30 nucleotides depending upon the target sequence whose expression is to be reduced and (ii) further wherein nucleotides 184 to 203 of SEQ ID NO:14 are replaced by a second variable nucleotide subsequence ranging in size from about 19 to about 30 nucleotides, said second variable nucleotide subsequence being capable of hybridizing to the first variable subsequence of the precursor miRNA; and d) an isolated nucleic acid fragment comprising a precursor miRNA said precursor miRNA corresponding substantially to the deoxyribonucleotide sequence set forth in SEQ ID NO:15 (i) wherein nucleotides 83 to 103 of SEQ ID NO:15 are replaced by a first variable nucleotide subsequence ranging in size from about 19 to about 30 nucleotides depending upon the target sequence whose expression is to be reduced and (ii) further wherein nucleotides 172 to 192 of SEQ ID NO:15 are replaced by a second variable nucleotide subsequence ranging in size from about 19 to about 30 nucleotides, said second variable nucleotide subsequence being capable of hybridizing to the first variable subsequence of the precursor miRNA.

Any of these isolated nucleic acid fragments can the be used to make a recombinant construct comprising these isolated nucleic acid fragments operably linked to at least one regulatory sequence.

These constructs can be transformed into plant cell so that the transformed plant cell comprises the recombinant construct in its genome.

In another aspect, this invention concerns a method for reducing expression of a target gene in a plant cell, said method comprising:

(a) transforming at least one plant cell with a nucleic acid construct comprising any of the isolated nucleic acid fragments described herein; and (b) selecting those transformed plant cell(s) whose level of expression of the target sequence is reduced when compared to the level of expression of the target gene in a wild type plant cell.

DETAILED DESCRIPTION

Information pertinent to this application can be found in U.S. patent application Ser. Nos. 10/963,238 and 10/963,394, filed Oct. 12, 2004. The entire contents of the above applications are herein incorporated by reference.

Other references that may be useful in understanding the invention include U.S. patent application Ser. No. 10/883,374, filed Jul. 1, 2004; U.S. patent application Ser. No. 10/913,288, filed Aug. 6, 2004; and U.S. patent application Ser. No. 11/334,776, filed Jan. 6, 2006.

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms and abbreviations are used. The following definitions are provided.

"microRNA or miRNA" refers to oligoribonucleic acid, which regulates expression of a polynucleotide comprising the target sequence. microRNAs (miRNAs) are noncoding RNAs of about 19 to about 24 nucleotides (nt) in length that have been identified in both animals and plants (Lagos-Quintana et al., *Science* 294:853-858 2001, Lagos-Quintana et al., *Curr. Biol.* 12:735-739 2002; Lau et al., *Science* 294:858-862 2001; Lee and Ambros, *Science* 294:862-864 2001; Llave et al., *Plant Cell* 14:1605-1619 2002; Mourelatos et al., *Genes. Dev,* 16:720-728 2002; Park et al., *Curr. Biol.* 12:1484-1495 2002; Reinhart et al., *Genes. Dev.* 16:1616-1626 2002) which regulates expression of a polynucleotide comprising the target sequence. They are processed from longer precursor transcripts that range in size from approximately 70 to 2000 nt or longer, and these precursor transcripts have the ability to form stable hairpin structures. In animals, the enzyme involved in processing miRNA precursors is called Dicer, an RNAse III-like protein (Grishok et al., *Cell* 106:23-34 2001; Hutvagner et al., *Science* 293:834-838 2001; Ketting et al., *Genes. Dev.* 15:2654-2659 2001). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al., *Curr. Biol.* 12:1484-1495 2002; Reinhart et al., *Genes. Dev.* 16:1616-1626 2002). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 2001; Lee et al., *EMBO J* 21:4663-4670 2002). Recent work has also examined the selection of the miRNA strand from the dsRNA product arising from processing of the hairpin by DICER (Schwartz et al., 2003, Cell 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

"pri-miRNAs" or "primary miRNAs" are long, polyadenylated RNAs transcribed by RNA polymerase II that encode miRNAs. "pre-miRNAs" are primary miRNAs that have been processed to form a shorter sequence that has the capacity to form a stable hairpin and is further processed to release a miRNA. In plants both processing steps are carried out by dicerlike and it is therefore difficult to functionally differentiate between "pri-miRNAs" and "pre-miRNAs". Therefore, a precursor miRNA, or a primary miRNA, is functionally defined herein as a nucleotide sequence that is capable of producing a miRNA. Given this functional definition, and as will be clear from the Examples and discussion herein, a precursor miRNA, primary miRNA and/or a miRNA of the invention can be represented as a ribonucleic acid or, alternatively, in a deoxyribonucleic acid form that "corresponds substantially" to the precursor miRNA, primary miRNA and/or miRNA. It is understood that the DNA in its double-stranded form will comprise a strand capable of being transcribed into the miRNA precursor described. Expression constructs, recombinant DNA constructs, and transgenic organisms incorporating the miRNA encoding DNA that results in the expression of the described miRNA precursors are described.

A "variable nucleotide subsequence" refers to a portion of a nucleotide sequence that replaces a portion of a pre-miRNA sequence provided that this subsequence is different from the sequence that is being replaced, i.e, it cannot be the same sequence.

A "target gene" refers to a gene that encodes a target RNA, ie., a gene from which a target RNA is transcribed. The gene may encode mRNA, tRNA, small RNA, etc.

A "target sequence" refers to an RNA whose expression is to be modulated, e.g., down-regulated. The target sequence may be a portion of an open reading frame, 5' or 3' untranslated region, exon(s), intron(s), flanking region, etc.

A "star sequence" is the complementary sequence within a miRNA precursor that forms a duplex with the miRNA. The complementarity of the star sequence does not need to be perfect. Non-helix disrupting substitutions (i.e. G:T base pairs etc.) are sometimes found, as well as 1-3 mismatches.

The term "genome" refers to the following: (1) the entire complement of genetic material (genes and non-coding sequences) present in each cell of an organism, or virus or organelle; (2) a complete set of chromosomes inherited as a (haploid) unit from one parent.

"Progeny" comprises any subsequent generation of a plant. Progeny will inherit, and stably segregate, genes and transgenes from its parent plant(s).

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used here "suppression" or "silencing" or "inhibition" are used interchangeably to denote the down-regulation of the expression of a product of a target sequence relative to its normal expression level in a wild type organism. Suppression includes expression that is decreased by about 10%, 15%, 20%, 25%, 30%, 35%, 40%, 45%, 50%, 55%, 60%, 65%, 70%, 75%, 80%, 85%, 90%, 95%, or 100% relative to the wild type expression level.

As used herein, "encodes" or "encoding" refers to a DNA sequence which can be processed to generate an RNA and/or polypeptide.

As used herein, "expression" or "expressing" refers to production of a functional product, such as, the generation of an RNA transcript from an introduced construct, an endogenous DNA sequence, or a stably incorporated heterologous DNA sequence. The term may also refer to a polypeptide produced from an mRNA generated from any of the above DNA precursors. Thus, expression of a nucleic acid fragment may refer to transcription of the nucleic acid fragment (e.g., transcription resulting in mRNA or other functional RNA) and/or translation of RNA into a precursor or mature protein (polypeptide).

As used herein, "heterologous" with respect to a sequence means a sequence that originates from a foreign species, or, if from the same species, is substantially modified from its native form in composition and/or genomic locus by deliberate human intervention. For example, with respect to a nucleic acid, it can be a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention.

The term "host cell" refers to a cell which contains or into which is introduced a nucleic acid construct and supports the replication and/or expression of the construct. Host cells may be prokaryotic cells such as *E. coli*, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The term "plant parts" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into ac ell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "genome" as it applies to a plant cells encompasses not only chromosomal DNA found within the nucleus, but organelle DNA found within subcellular components (e.g., mitochondrial, plastid) of the cell.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "domain" or "functional domain" refer to nucleic acid sequence(s) that are capable of eliciting a biological response in plants. The present invention concerns miRNAs composed of at least 21 nucleotide sequences acting either individually, or in concert with other miRNA sequences, therefore a domain could refer to either individual miRNAs or groups of miRNAs. Also, miRNA sequences associated with their backbone sequences could be considered domains useful for processing the miRNA into its active form. As used herein, "subdomains" or "functional subdomains" refer to subsequences of domains that are capable of eliciting a biological response in plants. A miRNA could be considered a subdomain of a backbone sequence. "Contiguous" sequences or domains refer to sequences that are sequentially linked without added nucleotides intervening between the domains. An example of a contiguous domain string is found in SEQ ID NO:7957 which represents SEQ ID NOs: 1-2652 as a continuous string that can be thought of as 2652 miRNA sequences linked together in a sequential concatenation.

RNA interference refers to the process of sequence-specific post-transcriptional gene silencing in animals mediated by short interfering RNAs (siRNAs) (Fire et al., *Nature* 391:806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as "dicer". Dicer is involved in the processing of the dsRNA into short pieces of dsRNA known as short interfering RNAs (siRNAs) (Berstein et al., *Nature* 409:363 2001) and/or pre miRNAs into miRNAs. Short interfering RNAs derived from dicer activity are typically about 21 to about 23 nucleotides in length and comprise about 19 base pair duplexes (Elbashir et al., *Genes Dev.* 15:188 2001). Dicer has also been implicated in the excision of 21- and 22-nucleotide small temporal RNAs (stRNAs) from precursor RNA of conserved structure that are implicated in translational control (Hutvagner et al., 2001, *Science* 293:834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al., *Genes Dev.* 15:188 2001). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Alishire, *Science* 297:1818-1819 2002; Volpe et al., *Science* 297:1833-1837 2002; Jenuwein, *Science* 297:2215-2218 2002; and Hall et al., *Science* 297:2232-2237 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 1998) were the first to observe RNAi in *C. elegans*. Wianny and Goetz (*Nature Cell Biol.* 2:70 1999) describe RNAi mediated by dsRNA in mouse embryos. Hammond et al. (*Nature* 404:293 2000) describe RNAi in *Drosophila* cells transfected with dsRNA. Elbashir et al., (*Nature* 411:494 2001) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 2001, Lagos-Quintana et al., *Curr. Biol.* 12:735-739 2002; Lau et al., *Science* 294:858-862 2001; Lee and Ambros, *Science* 294:862-864 2001; Llave et al., *Plant Cell* 14:1605-1619 2002; Mourelatos et al., *Genes. Dev.* 16:720-728 2002; Park et al., *Curr. Biol.* 12:1484-1495 2002; Reinhart et al., *Genes. Dev.* 16:1616-1626 2002). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., *Cell* 106:23-34 2001; Hutvagner at al., *Science* 293:834-838 2001; Ketting et al., *Genes. Dev.* 15:2654-2659 2001). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al., *Curr. Biol.* 12:1484-1495 2002; Reinhart et al., *Genes. Dev.* 16:1616-1626 2002). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 2001; Lee et al., *EMBO J* 21:4663-4670 2002). Recent work has also examined the selection of the miRNA strand from the dsRNA product arising from processing of the hairpin by DICER (Schwartz et al., 2003, Cell 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

In animals, there is direct evidence indicating a role for specific miRNAs in development. The lin-4 and let-7 miRNAs in *C. elegans* have been found to control temporal development, based on the phenotypes generated when the genes producing the lin-4 and let-7 miRNAs are mutated (Lee et al., *Cell* 75:843-854 1993; Reinhart et al., *Nature* 403-901-906 2000). In addition, both miRNAs display a temporal expression pattern consistent with their roles in developmental timing. Other animal miRNAs display developmentally regulated patterns of expression, both temporal and tissue-specific (Lagos-Quintana et al., *Science* 294:853-853 2001, Lagos-Quintana et al., *Curr. Biol.* 12:735-739 2002; Lau et al., *Science* 294:858-862 2001; Lee and Ambros, *Science* 294:862-864 2001), leading to the hypothesis that miRNAs may, in many cases, be involved in the regulation of important developmental processes. Likewise, in plants, the differential expression patterns of many miRNAs suggests a role in development (Llave et al., *Plant Cell* 14:1605-1619 2002; Park et al., *Curr. Biol.* 12:1484-1495 2002; Reinhart et al., *Genes. Dev.* 16:1616-1626 2002). However, a developmental role for miRNAs has not been directly proven in plants, because to date there has been no report of a developmental phenotype associated with a specific plant miRNA.

MicroRNAs appear to regulate target genes by binding to complementary sequences located in the transcripts produced by these genes. In the case of lin-4 and let-7, the target sites are located in the 3' UTRs of the target mRNAs (Lee et *Cell* 75:843-854 1993; Wightman et al., *Cell* 75:855-862 1993; Reinhart et al., *Nature* 403:901-906 2000; Slack et al., *Mol. Cell* 5:659-669 2000), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 1999). On the other hand, recent evidence suggests that miRNAs can, in some cases, cause specific RNA cleavage of the target transcript within the target site (Hutvagner and Zamore, *Science* 297:2056-2060 2002; Llave et al., *Plant Cell* 14:1605-1619 2002). It seems likely that miRNAs can enter at least two pathways of target gene regulation: Protein downregulation and RNA cleavage. MicroRNAs entering the RNA cleavage pathway incorporated into an RNA-induced silencing complex (RISC) that is similar or identical to that seen for RNAi.

The present invention concerns an isolated nucleic acid fragment comprising a precursor miRNA said precursor miRNA corresponding substantially to the deoxyribonucleotide sequence set forth in SEQ ID NO:11 (i) wherein nucleotides 430 to 450 of SEQ ID NO:11 are replaced by a first variable nucleotide subsequence ranging in size from about 19 to about 30 nucleotides depending upon the target sequence whose expression is to be reduced and (ii) further wherein nucleotides 244 to 264 of SEQ ID NO:11 are replaced by a second variable nucleotide subsequence ranging in size from about 19 to about 30 nucleotides, said second variable nucleotide subsequence being capable of hybridizing to the first variable subsequence of the precursor miRNA.

This isolated nucleic acid fragment comprising a precursor miRNA may be also be referred to as a "miRNA backbone". It is well known by those skilled in the art that it is difficult to differentiate if a transcript is a full-length pri-miRNA or a pre-miRNA. Therefore, a precursor miRNA is functionally defined as a nucleotide sequence that is capable of producing a miRNA.

Other isolated nucleic fragments of interest include the following;

a) transcribed froman isolated nucleic acid fragment comprising a precursor miRNA said precursor miRNA corresponding substantially to the deoxyribonucleotide sequence set forth in SEQ ID NO:12 (i) wherein nucleotides 94 to 114 of SEQ ID NO:12 are replaced by a first variable nucleotide subsequence ranging in size from about 19 to about 30 nucleotides depending upon the target sequence whose expression is to be reduced and (ii) further wherein nucleotides 163 to 183 of SEQ ID NO:12 are replaced by a second variable nucleotide subsequence ranging in size from about 19 to about 30 nucleotides, said second variable nucleotide subsequence being capable of hybridizing to the first variable subsequence of the precursor miRNA;

b) an isolated nucleic acid fragment comprising a precursor miRNA said precursor miRNA corresponding substantially to the deoxyribonucleotide sequence set forth in SEQ ID NO:13 (i) wherein nucleotides 53 to 73 of SEQ ID NO:13 are replaced by a first variable nucleotide subsequence ranging in size from about 19 to about 30 nucleotides depending upon the target sequence whose expression is to be reduced and (ii) further wherein nucleotides 97 to 117 of SEQ ID NO:13 are replaced by a second variable nucleotide subsequence ranging in size from about 19 to about 30 nucleotides, said second variable nucleotide subsequence being capable of hybridizing to the first variable subsequence of the precursor miRNA;

c) an isolated nucleic acid fragment comprising a precursor miRNA said precursor miRNA corresponding substantially to the deoxyribonucleotide sequence set forth in SEQ ID NO:14 (i) wherein nucleotides 110 to 130 of SEQ ID NO:14 are replaced by a first variable nucleotide subsequence ranging in size from about 19 to about 30 nucleotides depending upon the target sequence whose expression is to be reduced and (ii) further wherein nucleotides 184 to 203 of SEQ ID NO:14 are replaced by a second variable nucleotide subsequence ranging in size from about 19 to about 30 nucleotides, said second variable nucleotide subsequence being capable of hybridizing to the first variable subsequence of the precursor miRNA; and d) an isolated nucleic acid fragment comprising a precursor miRNA said precursor miRNA corresponding substantially to the deoxyribonucleotide sequence set forth in SEQ ID NO:15 (i) wherein nucleotides 83 to 103 of SEQ ID NO:15 are replaced by a first variable nucleotide subsequence ranging in size from about 19 to about 30 nucleotides depending upon the target sequence whose expression is to be reduced and (ii) further wherein nucleotides 172 to 192 of SEQ ID NO:15 are replaced by a second variable nucleotide subsequence ranging in size from about 19 to about 30 nucleotides, said second variable nucleotide subsequence being capable of hybridizing to the first variable subsequence of the precursor miRNA.

Any of these isolated nucleic acid fragments can the be used to make a recombinant construct comprising these isolated nucleic acid fragments operably linked to at least one regulatory sequence.

These constructs can be transformed into plant cell so that the transformed plant cell comprises the recombinant construct in its genome. Preferably, the plant cell can be a monocot plant cell. Examples of monocot plant cells include, but are not limited to, maize, sorghum, wheat, rice, oat, rye, barley, sugarcane, millet, bamboo, banana and orchid The most preferred monocot plant cell is maize.

In another aspect, this invention concerns a method for reducing expression of a target sequence in a plant cell, said method comprising:

(a) transforming at least one plant cell with a nucleic acid construct comprising a comprising any of the isolated nucleic acid fragments described herein; and (b) selecting those transformed plant cell(s) whose level of expression of the target sequence is reduced when compared to the level of expression of the target sequence in a wild type plant cell.

Bioinformatic approaches have been successfully used to predict targets for plant miRNAs (Llave et al., *Plant Cell* 14:1605-1619 2002; Park et al., *Curr. Biol.* 12:1484-1495 2002; Rhoades et al., *Cell* 110:513-520 2002), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

General categories of sequences of interest include, for example, those genes involved in regulation or information, such as zinc fingers, transcription factors, homeotic genes, or cell cycle and cell death modulators, those involved in communication, such as kinases, and those involved in housekeeping, such as heat shock proteins.

Target sequences may include coding regions and non-coding regions such as promoters, enhancers, terminators, introns and the like.

The target sequence may be an endogenous sequence, or may be an introduced heterologous sequence, or transgene. For example, the methods may be used to alter the regulation or expression of a transgene, or to remove a transgene or other introduced sequence such as an introduced site-specific recombination site. The target sequence may also be a sequence from a pathogen, for example, the target sequence may be from a plant pathogen such as a virus, a mold or fungus, an insect, or a nematode. A miRNA could be expressed in a plant which, upon infection or infestation, would target the pathogen and confer some degree of resistance to the plant.

In plants, other categories of target sequences include genes affecting agronomic traits, insect resistance, disease resistance, herbicide resistance, sterility, grain characteristics, and commercial products. Genes of interest also included those involved in oil, starch, carbohydrate, or nutrient metabolism as well as those affecting, for example, kernel size, sucrose loading, and the like. The quality of grain is reflected in traits such as levels and types of oils, saturated and unsaturated, quality and quantity of essential amino acids, and levels of cellulose. For example, genes of the phytic acid biosynthetic pathway could be suppressed to generate a high available phosphorous phenotype. See, for example, phytic acid biosynthetic enzymes including inositol polyphosphate kinase-2 polynucleotides, disclosed in WO 02/059324, inositol 1,3,4-trisphosphate 5/6-kinase polynucleotides, disclosed in WO 03/027243, and myo-inositol 1-phosphate synthase and other phytate biosynthetic polynucleotides, disclosed in WO 99/05298, all of which are herein incorporated by reference. Genes in the lignification pathway could be suppressed to enhance digestibility or energy availability. Genes affecting cell cycle or cell death could be suppressed to affect growth or stress response. Genes affecting DNA repair and/or recombination could be suppressed to increase genetic variability. Genes affecting flowering time could be suppressed, as well as genes affecting fertility. Any target sequence could be suppressed in order to evaluate or confirm its role in a particular trait or phenotype, or to dissect a molecular, regulatory, biochemical, or proteomic pathway or network.

A number of promoters can be used. These promoters can be selected based on the desired outcome. It is recognized that different applications will be enhanced by the use of different promoters in plant expression cassettes to modulate the timing, location and/or level of expression of the miRNA. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures each of these are incorporated herein by reference in their entirety.

In some embodiments it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the polynucleotides. Such wound-inducible promoters include potato proteinase inhibitor (pin II) gene (Ryan (1990) *Ann. Rev. Phytopath.* 28:425-449; Duan et al. (1996) *Nature Biotech.* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohrneier et al. (1993) *Plant Mol. Biol.* 22:783-792; Eckelkamp et al. (1993) *FEBS Lett.* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58. Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-

443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teen et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

Transformation protocols as well as protocols for introducing nucleotide sequences into plants may vary depending on the type of plant or plant cell, i.e., monocot or dicot, targeted for transformation. Suitable methods of introducing the DNA construct include microinjection (Crossway et al. (1986) *Biotechniques* 4:320-334; and U.S. Pat. No. 6,300,543), sexual crossing, electroporation (Riggs et al. (1986) *Proc. Natl. Acad. Sci. USA* 83:5602-5606), *Agrobacterium*-mediated transformation (Townsend et al., U.S. Pat. No. 5,563,055; and U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Sidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); and U.S. Pat. No. 5,736,369 (meristem transformation), all of which are herein incorporated by reference.

The nucleotide constructs may be introduced into plants by contacting plants with a virus or viral nucleic acids. Generally, such methods involve incorporating a nucleotide construct of the invention within a viral DNA or RNA molecule. Further, it is recognized that useful promoters encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In some embodiments, transient expression may be desired. In those cases, standard transient transformation techniques may be used. Such methods include, but are not limited to viral transformation methods, and microinjection of DNA or RNA, as well other methods well known in the art.

The cells from the plants that have stably incorporated the nucleotide sequence may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic imparted by the nucleotide sequence of interest and/or the genetic markers contained within the target site or transfer cassette. Two or more generations may be grown to ensure that expression of the desired phenotypic characteristic is stably maintained and inherited and then seeds harvested to ensure expression of the desired phenotypic characteristic has been achieved.

EXAMPLES

Example 1

Isolation of Genomic MicroRNA Precursor Genes

Sequences encoding maize microRNA genes as described in Zhang B, et al. (2006) *FEBS Lett.* 580:3753-62) were used as queries for BLAST analysis of the Pioneer Unicorn 6.0 collection of expressed sequence tags. Approximately 30% of the queries had exact matches in the Unicorn 6.0 collection. The following primers (purchased from MWG-BIOTECH Inc.) were designed to amplify a selection of five of these sequences (see Table 1).

TABLE 1

| Primers For Amplification of Genomic MicroRNA Precursors | | |
|---|---|---|
| Primer | Primer Sequence | SEQ ID NO |
| 159cs | 5'-ccatggcttttcatagcacctctatacctc-3' | 1 |
| 159ca | 5'-ggatccacgggcgctcgctgcacccagatcc-3' | 2 |
| 164hs | 5'-ggatcctgcgaagctgagtgcagacgtccg-3' | 3 |
| 164ha | 5'-ccatgggtacgagggacgatgggattaggc-3' | 4 |
| 168as | 5'-ggatccggttcgcgcggagggaaggagggag-3' | 5 |
| 168aa | 5'-ccatgggccaatcggctacttgatctcttcccc-3' | 6 |
| 169rs | 5'-ggatccctccacacagagaagcaaagaaacc-3' | 7 |
| 169ra | 5'-ccatgggtaacctatcgtctattcattttg-3' | 8 |
| 396hs | 5'-ggatccgtcccccagatttgctaggacacc-3' | 9 |
| 396ha | 5'-ccatggtgggcctgctactatgatgtttag-3' | 10 |

The 159 sense primer (159cs, SEQ ID NO:1) included nucleotides that encoded an Nco I site. The 159 antisense primer (159ca, SEQ ID NO:2) included nucleotides that encoded a Bam HI site. The remaining four sense primers (SEQ ID NOs:3, 5, 7, and 9) included nucleotides that encoded a Bam HI site. The remaining four antisense primers (SEQ ID NOs:4, 6, 8, and 10) included nucleotides that encoded an Nco I site.

*Zea mays* cv. B73 seeds were germinated and genomic DNA was made from seedling tissue using the Qiagen DNeasy Plant Maxi Kit according to the manufacture's instructions. DNA products were amplified using the genomic DNA as template and primers pairs above with ExTaq polymerase (TaKaRa Bio Inc.). The resulting DNA products were cloned into pCR2.1 (Invitrogen) and completely sequenced. The characterized microRNA precursors are summarized in Table 2.

TABLE 2

| MicroRNA Precursor Sequences | | |
|---|---|---|
| microRNA Precursor | SEQ ID NO | Length (nucs) |
| 159c | 11 | 875 |
| 164h | 12 | 780 |
| 168a | 13 | 791 |
| 169r | 14 | 859 |
| 396h | 15 | 633 |

Example 2

Design of Artificial MicroRNA Sequences

Artificial microRNAs (amiRNAs) that would have the ability to silence the maize gene phytoene desaturase (NCBI number U37285) were designed largely according to rules described in Schwab R, et al. (2005) *Dev Cell* 8: 517-27. To summarize, microRNA sequences are 21 nucleotides in length, start at their 5'-end with a "U", display 5' instability relative to their star sequence which is achieved by including a C or G at position 19, and their 10th nucleotide is either an "A" or an "U". An additional requirement for artificial microRNA design was that the amiRNA have a high free delta-G as calculated using the ZipFold algorithm (Markham, N. R. & Zuker, M. (2005) *Nucleic Acids Res.* 33: W577-W581.) Optionally, a one base pair change was added to the 5' portion of the amiRNA so that the sequence differed from the target sequence by one nucleotide. The amiRNAs that was used to silence the phytoene desaturase was 5'-ucagcagcaauuucaccagga-3' (the DNA sequence corresponding to this amiRNA is represented by SEQ ID NO:16). Two additional amiRNAs were designed to silence phytoene desaturase. These sequences are PDS 2, 5'-ugcaauaaaaaccucaucgua-3' (the DNA sequence corresponding to this amiRNA is represented by SEQ ID NO:35) and PDS 3, 5'-uacucgcaaaacaucucugag-3' (the DNA sequence corresponding to this amiRNA is represented by SEQ ID NO:36)

Example 3

Design of an Artificial Star Sequences

"Star sequences" are those that base pair with the amiRNA sequences, in the precursor RNA, to form imperfect stem structures. To form a perfect stem structure the star sequence would be the exact reverse complement of the amiRNA. The maize precursor sequence as described by Zhang et al. in Supplemental material Table S1 was folded using mfold (M. Zuker (2003) *Nucleic Acids Res.* 31: 3406-15; and D. H. Mathews, J. et al. (1999) *J. Mol. Biol.* 288: 911-940). The miRNA sequence was then replaced with the amiRNA sequence and the endogenous star sequence was replaced with the exact reverse complement of the amiRNA. Changes in the artificial star sequence were introduced so that the structure of the stem would remain the same as the endogenous structure. The altered sequence was then folded with mfold and the original and altered structures were compared by eye. If necessary, further alternations to the artificial star sequence were introduced to maintain the original structure. The DNA sequences corresponding to artificial star sequences that were used to silence the phytoene desaturase are:

TABLE 3

| Artificial microRNA Star Sequences | | |
|---|---|---|
| amiRNA precursor | Star Sequence | SEQ ID NO |
| 159c-PDS | tccaggtgaatttggtgctgt | 17 |
| 164h-PDS | tctggtgaaaacgctgctga | 18 |
| 168a-PDS | ccctggcaaaattgctgctga | 19 |
| 169r-PDS | gcctggtgaacattgctgctga | 20 |
| 396h-PDS | tcctggtgcaattgctgctga | 21 |
| 396h-PDS 2 | tacgatgacgtttttattgca | 37 |
| 396h-PDS 3 | ctcagagacgttttgcgagta | 38 |

Example 4

Conversion of Genomic MicroRNA Precursors to Artificial MicroRNA Precursors

Genomic miRNA precursor genes are converted to amiRNAs using overlapping PCR and the resulting DNAs are completely sequenced. These DNAs are then cloned downstream of an appropriate promoter in a vector capable of maize transformation. The resulting plasmids are then co integrated into *Agrobacterium* strain LBA4404 with vir plasmid PHP10523 (PCT Publication No. WO2002/004,649 published Jan. 17, 2002) and can be used for transformation of maize.

Alternatively, amiRNAs can be synthesized commercially, for example by Codon Devices, (Cambridge, Mass.). The synthesized DNA is then cloned downstream of an appropriate promoter in a vector capable of maize transformation. The resulting plasmids are then co integrated into *Agrobacterium* strain LBA4404 with plasmid PHP10523 and can be used for transformation of maize.

Example 5

Conversion of Genomic MicroRNA Precursors to Artificial MicroRNA Precursors

Genomic miRNA precursor genes were converted to amiRNA precursors using overlapping PCR as described in example 4 and the resulting DNAs were completely sequenced. The following five amiRNAs precursors were made:

TABLE 4

Artificial MicroRNA Precursor Sequences Targeting Phytoene Desaturase

| microRNA Precursor | SEQ ID NO | Length (nucs) |
|---|---|---|
| 159c-PDS | 22 | 684 |
| 164h-PDS | 23 | 739 |
| 168a-PDS | 24 | 791 |
| 169r-PDS | 25 | 860 |
| 396h-PDS | 26 | 633 |

These DNAs were then cloned downstream of the ubiquitin promoter-intron of PHP23576. PHP23576 contains Gateway (Invitrogen) L1 and L2 sites. The resulting plasmids were then recombined with plasmid PHP20622 (PCT Publication No. WO2006/107,931 published Oct. 12, 2006). The resulting plasmids were then co integrated into Agrobacterium strain LBA4404 with vir plasmid PHP10523 and used for transformation of maize.

Example 6

Transformation of Maize

A. Maize Particle-Mediated DNA Delivery

A DNA construct can be introduced into maize cells capable of growth on suitable maize culture medium. Such competent cells can be from maize suspension culture, callus culture on solid medium, freshly isolated immature embryos or meristem cells. Immature embryos of the Hi-II genotype can be used as the target cells. Ears are harvested at approximately 10 days post-pollination, and 1.2-1.5 mm immature embryos are isolated from the kernels, and placed scutellum-side down on maize culture medium.

The immature embryos are bombarded from 18-72 hours after being harvested from the ear. Between 6 and 18 hours prior to bombardment, the immature embryos are placed on medium with additional osmoticum (MS basal medium, Musashige and Skoog, 1962, *Physiol. Plant* 15:473-497, with 0.25 M sorbitol). The embryos on the high-osmotic medium are used as the bombardment target, and are left on this medium for an additional 18 hours after bombardment.

For particle bombardment, plasmid DNA (described above) is precipitated onto 1.8 mm tungsten particles using standard CaCl2-spermidine chemistry (see, for example, Klein et al., 1987, *Nature* 327:70-73). Each plate is bombarded once at 600 PSI, using a DuPont Helium Gun (Lowe et al., 1995, *Bio/Technol* 13:677-682). For typical media formulations used for maize immature embryo isolation, callus initiation, callus proliferation and regeneration of plants, see Armstrong, C., 1994, In "The Maize Handbook", M. Freeling and V. Walbot, eds. Springer Verlag, NY, pp 663-671.

Within 1-7 days after particle bombardment, the embryos are moved onto N6-based culture medium containing 3 mg/l of the selective agent bialaphos. Embryos, and later callus, are transferred to fresh selection plates every 2 weeks. The calli developing from the immature embryos are screened for the desired phenotype. After 6-8 weeks, transformed calli are recovered.

B. Transformation of Maize Using *Agrobacterium*

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of TO plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C.

in the light (about 80 μE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000X Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 μM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L Gelrite®, 100 μM acetosyringone (filter-sterilized), pH 5.8.
3. PHI-C: PHI-B without Gelrite® and acetosyringonee, reduce 2,4-D to 1.5 mg/L and supplemented with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 μg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into a maize inbred line either by direct transformation or introgression from a separately transformed line.

Transgenic plants, either inbred or hybrid, can undergo more vigorous field-based experiments to study expression effects.

Example 7

Assay of PDS Phenotype and Results

Nine-to-ten day after-pollination embryos were infected with *Agrobacterium* as described above and selected on Basta. Five different infections were carried out, each with an Agrobacterium containing one of the five amiRNAs described in example five. Somatic embryos were regenerated and arrayed in a 3×3 grid. A single layer of plates containing the arrayed plantlets was exposed to ~114 mEinsteins m-2 sec-1 of light. The plantlet in the middle of the grid was visually scored for phenotype as either "green", "white" or "pale". Percentage silencing is the summation of the percentage white plants and the percentage of pale plants. Typically, 50 individual events were scored for each construct.

TABLE 5

Silencing Efficacy of amiRNAs

| construct # | amiRNA | % white plants | % pale | % silencing |
|---|---|---|---|---|
| PHP30223 | 159c-PDS | 0.0 | 14.3 | 14 |
| PHP30448 | 164h-PDS | 0.0 | 7.6 | 8 |
| PHP30225 | 168a-PDS | no data | no data | no data |
| PH P30451 | 169r-PDS | 10.9 | 47.3 | 58 |
| PHP30452 | 396h-PDS | 13.0 | 59.3 | 76 |
| PHP33006 | 396h-PDS | 248.3% | 41.4% | 90 |
| PHP33007 | 396h-PDS | 318.3% | 68.4% | 87 |

These results show that some of the amiRNA precursors are capable of producing amiRNAs that are effective in gene silencing. The two additional miRNAs, targeting phytoene desaturase, were cloned into the 396h backbone along with their star sequences. Both constructs showed silencing efficacy similar to PHP30452 shown in Table 5.

Example 8

Northern Blot Analysis

RNA was prepared from frozen seedling tissue using Trizol (Invitrogen) according to the protocol provided by the manufacturer. Total RNA was run on a 15% TBE-Urea PAGE gel, run at 200V in 0.5× TBE for approximately 60 to 90 minutes and then transferred to a BrightStar-Plus Positive Charged Nylon Membrane (Ambion) using a Trans-Blot SD cell. After transfer, the blot was washed with 0.5× TBE and the RNA was cross linked to the membrane using one cycle on Auto-Energy in a Stratalinker (Stratagene). The Blot was pre-hybridized in ULTRAhyb-oligo Hybridization Buffer (Ambion) for 30 minutes at 42 degree C. and then hybridized overnight at 42 degree in ULTRAhyb-oligo Hybridization Buffer with the addition of a biotin labeled probe. The biotin labeled probe was a concatamer of the two copies of the reverse complement of the amiRNA sequence separated by a 4 bp spacer and was labeled using BrightStar Psoralen-Biotin Nonisotopic Labeling Kit (Ambion). After hybridization the blot was washed with the NorthernMax Wash Solution (Ambion) and detection was carried out using BrightStar BioDetect Nonisotopic Detection Kit (Ambion) according to the protocol provided by the manufacturer. In all cases, presence of the 21 bp amiRNA sequence correlated with the phenotype. Furthermore, moderate levels of signal correlated with pale plants while greater levels of signal correlated with white plants.

Example 9

Truncated Artificial MicroRNA Precursors are Capable of Silencing Genes

In an attempt to determine whether constructs that contained less then full full-length Artificial MicroRNA Precursors are capable of silencing genes the following shortened amiRNA precursors were made using PCR.

TABLE 6

Truncated Artificial MicroRNA Precursors Targeting Phytoene Desaturase

| microRNA Precursor | SEQ ID NO | Length (nucs) |
|---|---|---|
| 169r-PDS-sht | 27 | 96 |
| 169r-PDS-med | 28 | 305 |
| 396h-PDS-sht | 29 | 117 |
| 396h-PDS-med | 30 | 292 |

These shortened amiRNA constructs were completely sequenced and cloned into constructs as described in Example 5. These constructs were transformed into maize embryos and scored for their ability to silence PDS.

TABLE 7

Silencing Efficacy of Truncated amiRNAs

| construct # | amiRNA | % white plants | % pale | % silencing |
|---|---|---|---|---|
| PHP32347 | 169r-PDS-sht | 0.00 | 0.00% | 0 |
| PHP32346 | 169r-PDS-med | 0.00 | 33.9 | 33.9 |
| PHP32349 | 396h-PDS-sht | 0.00 | 0.00 | 0 |
| PHP32348 | 396h-PDS-med | 5.2 | 29.3 | 34.5 |

These results show the shortened constructs are capable of producing amiRNAs. However if the construct is shortened too much it is no longer competent to produce amiRNAs.

Example 10

Artificial microRNAs to Silence fad2-1

The above examples show the silencing of the maize PDS gene, but it is known to those skilled in the art that amiRNAs can be constructed to silence many genes. As an example of another gene that can be silenced an amiRNA targeting fad2-1 was designed as described in Example 2, artificial star sequences were designed as described in Example 3 and amiRNA precursors were created as explained in Example 4. These constructs are summarized in Table 8.

TABLE 8

Artificial MicroRNA Precursors Targeting Fatty Acid Desaturase

| microRNA Precursor | SEQ ID NO | Length (nucs) |
|---|---|---|
| 159c-FAD | 31 | 684 |
| 168a-FAD | 32 | 790 |
| 169r-FAD | 33 | 861 |
| 396h-FAD | 34 | 633 |

These DNAs were then cloned downstream of the *Zea mays* 16 KD oleosin gene promoter containing the 5' UTR in the plasmid PHP20790. PHP20790 contains Gateway (Invitrogen) L1 and L2 sites. The resulting plasmids were then recombined with plasmid PHP20622. The resulting plasmids were then co integrated into *Agrobacterium* strain LBA4404 with plasmid PHP10523 and used for transformation of maize embryos from cultivar GS3 pollinated with pollen from cultivar HC69. Plants were allowed to regenerate and were crossed using the transgenic plant as a female and HC69 as a male. Seeds were collected and were analyzed for fatty acid content using standard methods.

GC analysis of FAME was employed to investigate if amiRNA expression alters the fatty acid profile of maize seed. Approximately 50 seeds were analyzed per event and 18-25 events were analyzed per construct. Hexane, 1.5 mL, was added to crushed maize in an extraction tray. The hexane with dissolved oil was transferred to 1.8 mL glass GC vials. To which 100 μL trimethylsulfonium hydroxide was added for transesterification. Fatty acid methyl esters (1 μL injected from hexane layer, split ratio 80 to 1) were separated and quantified using a Agilent 6890 Gas Chromatograph fitted with a 15 m Zebron ZB-wax capillary column, I.D. 0.25 mm, film thickness 0.25 μm. (Catalog #7EG-G007-11, Phenomenex). The oven temperature was isothermal 220° C. for 2.5 min. Carrier gas was standard grade helium. Retention times were compared to those for methyl esters of standards commercially available (Nu-Chek Prep, Inc.). General approaches to altering and analyzing oils in maize by down-regulating fatty acid desaturase pathways can be found in U.S. patent application Ser. No. 10/223,646. Results are summarized in Table 9.

Constructs with the 168a backbone and the 396h backbone gave efficient silencing. Constructs made containing the 159c backbone and the 169r backbone did not give any silencing (% silencing fad2-1; which is the percentage of events showing silencing).

Successive generations of transgenic seeds were planted in the field and T2 and T3 seeds were assayed for fatty acid content. The effect of these constructs was shown to be heritable and stable.

When compared to the silencing achieved with the amiRNA targeting PDS (% silencing PDS in Table 9) it appears that some miRNA precursor backbones silence in multiple tissue types (396h, and potentially 164h), while others are more specific in which tissues they are effective (159c and 169r). All of the five miRNA backbones showed efficacy in at least one tissue type.

TABLE 9

Artificial miRNA precursors exhibit selective efficacy

| Backbone | SEQ ID NO | % silencing PDS | % silencing fad2-1 |
|---|---|---|---|
| 159c | 22, 31 | 14 | 0 |
| 164h | 23, none | 8 | no data |
| 168a | 24, 32 | no data | 85 |
| 169r | 25, 33 | 58 | 0 |
| 396h | 26, 34 | 76 | 92 |

Possible explanations for the results presented in Table 9 include, but are not limited to, differential stability of miRNA precursors in temporal, spatial or organ-specific manners; differential processing of the miRNA precursors (support for differential post-transcriptional processing steps for miRNA has been discovered in animal systems Obernosterer et al. (2007) *RNA* 12: 1161-1167); or differential competition for the dicer complex among miRNA populations.

Example 11

Artificial microRNAs to Silence Lethal Leaf Spot

The above examples show the silencing of the maize PDS gene and fad2 gene, but it is known to those skilled in the art that amiRNAs can be constructed to silence many genes. As an example of another gene that can be silenced an amiRNA targeting lethal leaf spot was designed as described in Example 2, the microRNA is 5'-uuugaaaggacgguguaaggc-3' (the DNA sequence corresponding to this amiRNA is represented by SEQ ID NO:35). Artificial star sequences were designed as described in Example 3 and are shown in Table 10. amiRNA precursors were created as explained in Example 4.

TABLE 10

| Artificial microRNA Star Sequences | | |
|---|---|---|
| amiRNA precursor | Star Sequence | SEQ ID NO |
| 168a-IIs | accttaatccgtcctttcaaa | 36 |
| 69r-IIs | cccttacacctgtcctttcaac | 37 |
| 396h-IIs | gccttacagcgtcctttcaaa | 38 |

Maize plants in which the gene lethal leaf spot (NCBI number, U77345; Gray J et al. (1997) A novel suppressor of cell death in plants encoded by the Lls1 gene of maize. Cell. April 4; 89(1):25-31.) has been silenced show a phenotype of dead lesions throughout developing leaves and, in some cases, death of the plant. The % of silencing was determined by a visual examination of plants approximately 8 weeks after the plants were transferred to the greenhouse. All three constructs gave efficient silencing (Table 11).

TABLE 11

| Artificial mIRNA constructs efficiently silence lethal leaf spot | | |
|---|---|---|
| PHP Number | construct | % silencing |
| PHP36155 | 168a-IIs | 82 |
| PHP 33788 | 69r-IIs | 80 |
| PHP 36154 | 396h-IIs | 85 |

Example 12

Artificial microRNAs to Both Fatty Acid Desaturase and Multidrug Resistant Protein At times it is desirable to silence more than one gene with a given construct. Individual amiRNA precursors can be operably linked to the same or different promoters. Alternatively, two or more amiRNA precursors can be operably linked to each other and then linked to one promoter. From such a construct two or more amiRNAs would be produced.

Constructs containing artificial microRNAs to silence fad2-1 are shown in example 10. As an example of another gene that can be silenced an amiRNA targeting multi-drug resistant protein (MRP) was designed as described in Example 2, the microRNA is 5'-uaauucacaaucucaccacuc-3' (the DNA sequence corresponding to this amiRNA is represented by SEQ ID NO:39). Artificial star sequences were designed as described in Example 3 and are shown in Table 12. Two MRP amiRNA precursor were created, 168a-MRP (SEQ ID No:42) and 396h-MRP (SEQ ID No:43) as explained in Example 4. Silencing of MRP results in a reduction of phytic acid (Shi J. et al. (2007) Embryo-specific silencing of a transporter reduces phytic acid content of maize and soybean seeds. Nat Biotechnol. August; 25(8):930-7.)

TABLE 12

| Artificial microRNA Star Sequences | | |
|---|---|---|
| amiRNA precursor | Star Sequence | SEQ ID NO |
| 168a-MRP | aagtggctagattgtgaatta | 40 |
| 396h-MRP | gagtggtgacattgtgaatta | 41 |

These precursors were cloned either upstream or downstream of fad 2 precursors (described in Example 10) to created cassettes and then cloned into constructs and transferred to Agrobacterium to created the constructs described in Table 13 as previously described. Maize transformation was performed as described in Example 6 and transgenic seeds will be assayed for both phytate and fatty acid content.

TABLE 13

| Artificial miRNA constructs containing amiRNAs designed to silence both fad 2-1 and MRP | |
|---|---|
| PHP Number | construct |
| PHP38380 | 168aFAD2-1/168a-MRP |
| PHP38381 | 396h-Fad2-1/168a-MRP |
| PHP38382 | 168a-MRP/396h-FAD2-1 |
| PHP38383 | 396h-MRP/396h-FAD2-1 |

What is claimed is:

1. An isolated nucleic acid fragment comprising the deoxyribonucleotide sequence set forth in SEQ ID NO:13 wherein (i) nucleotides 53 to 73 of SEQ ID NO:13 are replaced by a first variable nucleotide subsequence ranging in size from 19 to 24 nucleotides depending upon the target sequence whose expression is to be reduced, (ii) nucleotides 97 to 117 of SEQ ID NO:13 are replaced by a second variable nucleotide subsequence ranging in size from 19 to 24 nucleotides, said second variable nucleotide subsequence being capable of hybridizing to the first variable subsequence, and (iii) the precursor miRNA produced by said isolated nucleic acid fragment has the same stem structure as the precursor miRNA produced by endogenous SEQ ID NO:13.

2. A recombinant construct comprising the isolated nucleic acid fragment of claim 1 operably linked to at least one regulatory sequence.

3. A plant cell comprising the recombinant construct of claim 2.

4. The plant cell of claim 2 wherein the plant, cell is a monocot plant cell.

5. A method for reducing expression of a target sequence in a plant cell, said method comprising:

(a) transforming at least one plant cell with a nucleic acid construct comprising the deoxyribonucleotide sequence set forth in SEQ ID NO:13 wherein (i) wherein nucleotides 53 to 73 of SEQ ID NO:13 are replaced by a first variable nucleotide subsequence ranging in size from 19 to 24 nucleotides depending upon the target sequence whose expression is to be reduced, (ii) nucleotides 97 to 117 of SEQ ID NO:13 are replaced by a second variable nucleotide subsequence ranging in size from 19 to 24 nucleotides, said second variable nucleotide subsequence being capable of hybridizing to the first variable subsequence, and (iii) the precursor miRNA produced by said isolated nucleic acid fragment has the same stem structure as the precursor miRNA produced by endogenous SEQ ID NO:13; and (b) selecting those transformed plant cell(s) whose level of expression of the target sequence is reduced when compared to the level of expression of the target gene in a wild type plant cell.

6. The method of claim 5 wherein the plant cell is a monocot plant cell.

7. An artificial miRNA transcribed from the isolated nucleic acid fragment of claim 1.

* * * * *

SEQUENCE LISTING

```
<160> NUMBER OF SEQ ID NOS: 43

<210> SEQ ID NO 1
<211> LENGTH: 30
<212> TYPE: DNA
<213> ORGANISM: Artificial
<220> FEATURE:
<223> OTHER INFORMATION: DNA primer 159cs

<400> SEQUENCE: 1

ccatggcttt tcatagcacc tctatacctc                                   30


<210> SEQ ID NO 2
<211> LENGTH: 31
<212> TYPE: DNA
<213> ORGANISM: Artificial
<220> FEATURE:
```

<223> OTHER INFORMATION: DNA primer 159ca

<400> SEQUENCE: 2
ggatccacgg gcgctcgctg cacccagatc c 31

<210> SEQ ID NO 3
<211> LENGTH: 30
<212> TYPE: DNA
<213> ORGANISM: Artificial
<220> FEATURE:
<223> OTHER INFORMATION: DNA primer 164hs

<400> SEQUENCE: 3
ggatcctgcg aagctgagtg cagacgtccg 30

<210> SEQ ID NO 4
<211> LENGTH: 30
<212> TYPE: DNA
<213> ORGANISM: Artificial
<220> FEATURE:
<223> OTHER INFORMATION: DNA primer 164ha

<400> SEQUENCE: 4
ccatgggtac gagggacgat gggattaggc 30

<210> SEQ ID NO 5
<211> LENGTH: 31
<212> TYPE: DNA
<213> ORGANISM: Artificial
<220> FEATURE:
<223> OTHER INFORMATION: DNA primer 168as

<400> SEQUENCE: 5
ggatccggtt cgcgcggagg gaaggaggga g 31

<210> SEQ ID NO 6
<211> LENGTH: 33
<212> TYPE: DNA
<213> ORGANISM: Artificial
<220> FEATURE:
<223> OTHER INFORMATION: DNA primer 168aa

<400> SEQUENCE: 6
ccatgggcca atcggctact tgatctcttc ccc 33

<210> SEQ ID NO 7
<211> LENGTH: 31
<212> TYPE: DNA
<213> ORGANISM: Artificial
<220> FEATURE:
<223> OTHER INFORMATION: DNA primer 169rs

<400> SEQUENCE: 7
ggatccctcc acacagagaa gcaaagaaac c 31

<210> SEQ ID NO 8
<211> LENGTH: 30
<212> TYPE: DNA
<213> ORGANISM: Artificial
<220> FEATURE:
<223> OTHER INFORMATION: DNA primer 169ra

<400> SEQUENCE: 8
ccatgggtaa cctatcgtct attcattttg 30

<210> SEQ ID NO 9

<211> LENGTH: 30
<212> TYPE: DNA
<213> ORGANISM: Artificial
<220> FEATURE:
<223> OTHER INFORMATION: DNA primer 396hs

<400> SEQUENCE: 9
ggatccgtcc cccagatttg ctaggacacc 30

<210> SEQ ID NO 10
<211> LENGTH: 30
<212> TYPE: DNA
<213> ORGANISM: Artificial
<220> FEATURE:
<223> OTHER INFORMATION: DNA primer 396ha

<400> SEQUENCE: 10
ccatggtggg cctgctacta tgatgtttag 30

<210> SEQ ID NO 11
<211> LENGTH: 875
<212> TYPE: DNA
<213> ORGANISM: Zea mays

<400> SEQUENCE: 11
cttttcatag cacctctata cctcttcttc tcgtcgtcac tctatcccgc atctgctgtt 60
ctttatttct atacatacat atatactatc atcggttatt tgcttctcta ttctgtccga 120
gtactttacg gtgttccgca catagatctc gtggccggct gttttgcgct ttcgcttgcg 180
tttcttggcc ctgctggtgt tgaccggtcc gaacgggggc agatcgatgc tttgggtttg 240
aagcggagct cctatcattc caatgaaggg tcgttccgaa gggctggttc cgctgctcgt 300
tcatggttcc cactatccta tctcatcatg tgtatatatg taatccatgg gggagggttt 360
ctctcgtctt tgagataggc ttgtggtttg catgaccgag gagctgcacc gccccccttgc 420 tggccgctct ttggattgaa gggagctctg catcctgatc cacccctcca tttttttttg 480
cttgttgcgt ccttcctggg acctgagatc cgaggctcgt ggtggctcac tgtagcctcg 540
ctacactgtt ttcttctcct ctcctgtgct atttgctgtt tctcctaaga ttctttaggc 600
cgtgcttatc cgtgctggag tttaacgaag cagcacgttg ctgctgctgg tgctgccctc 660
atgccctggt ggtcgactgg tatcggtacc cgtacttgcg tcgctttatt ataccctatc 720
ttcgccggtg aggtttccgg ccgttcggta caggtagtct atgtcaaaca ctcgttttat 780
ttcttgtcat actatattct tctgcttcct gttcgtaccc ggcggcgtgt gcctttgcgg 840
tggcgctcct ggatctgggt gcagcgagcg cccgt 875

<210> SEQ ID NO 12
<211> LENGTH: 780
<212> TYPE: DNA
<213> ORGANISM: Zea mays

<400> SEQUENCE: 12
tgcgaagctg agtgcagacg tccgatcccc gatccatggc tccttttctg gcacttgaga 60
gatgtgtgtg tggtagacgg tggctgtgcg tggtggagaa gcagggcacg tgcattacca 120
tccaatgccg ccgggtgggt gggtggaatg gatggatggt tcttgatgtg cccatcttct 180
ccaccgagca cgaactgtct tggatccgcg cgcgcgtgcc gtacatacct cgtcatgcag 240
gagttcaggt gctgcctaat cctcggcggc cctcaccgcg ccaccggcgt ctcgcgtcgt 300
cgctgccgat cgatcgatcg tccagcccgc cgccagttga gttccgaacc ccgatgctta 360

-continued

```
tagcctccca tccctggtta gcaagcatcg tgtgtatctt gcatctcaga cttgcttcct    420

cttcatcatt cattcattca tactcaagca ttaattattc aggaccaagc aagcggtaga    480

attcaaattc aattcgcaca accctttgct tgtcagctag cttaccttgt gtattggatt    540

tgaatacatg ctggtaatcc atctaataag aaagcgctgt gtggcgctac ctgtccgtag    600

tatggccgcg ccgactgtct gtcggctggc atggcatgat atacattcta gttatcttga    660

accaaaggcg actgtccgta gagttgcttg ctcttgcttc agcaggtggg aatggcgccg    720

tgcacttggg ttcgcctgtc tcagttacca gaggagccta atcccatcgt ccctcgtacc    780
```

<210> SEQ ID NO 13
<211> LENGTH: 791
<212> TYPE: DNA
<213> ORGANISM: Zea mays

<400> SEQUENCE: 13

```
ggttcgcgcg gagggaagga gggagaagaa gcgaagccgc gccgcctcgg gctcgcttgg     60

tgcagatcgg gacccgccgc ccggccgacg ggacggatcc cgccttgcac caagtgaatc    120

ggagccggcg gagcgataca gcggccggcc gaccgccgcc tgcttgcctg cgcgcgctgc    180

tctcgactgc ggatgccgcc ctcggtttgt ttgtttgttt ttttctttct gataaggatc    240

gtgctgattg ctgtgactcc gtgtcgccgc ccgtgggaat tgttattagg cgccgtgggg    300

atctctgctc taggttagag taagcagtcc ggatctggat ctggcgcggg tccaaatttc    360

taacctctgg tgagacatct ccgtttttgt ggtgcggggt gcaaaatttg ccggtcatga    420

tgccactcgg atggatcacg gggaaaccat gcctaggtgg attattggtt cggcttcttt    480

taccgctagc ctaccacggg ctcacattgg ttgtaggttt tgtcttagat ttggctcgcc    540

caactgtagg acgaccgttg attggtctac ttgtgtaggt agattgcttg gtagagggga    600

ctcctttttt tctctcaaga aactacgccg gacttcccct gttacatgcg gcctcctgtg    660

tatgtgaggt gatgcgagtg gagtccttga tgaacactag aggctagaaa tccagtgatt    720

aggtgtccag gaatatatgc tcgggggatc agtcaagagg aggtggggaa gagatcaagt    780

agccgattgg c                                                          791
```

<210> SEQ ID NO 14
<211> LENGTH: 859
<212> TYPE: DNA
<213> ORGANISM: Zea mays

<400> SEQUENCE: 14

```
ccctccacac agagaagcaa agaaaccaca ccacagtcgt aggggaaggg agaggaggga     60

gggtggcttc tgctgggttg ccatgtgcta tgaggtagag aacgggatgc agccaaggat    120

gacttgccgg ctcctggaac ctggaggcgt ctcagcttgc tgtgctgtgg cttagaactt    180

agtcggcaag tctgtccttg gctacaccta gttctcttcc tctcgtgtat ggccctcaag    240

caccgtcaag agatctagga cctgcattca tatatcatca gcccactcca gaggaaacgt    300

aagggcaagt atgcatctaa cctcaagttg acatatttct atttctcctg caattttggg    360

tcttccaaaa aaatcagaaa tttgagatat atgaatatta ttacaaacat acagggcttg    420

catacaatac aagcccaagc cccatctggc atcatacgtc aaatttcata catgcatctg    480

tcagacaata tatatcctca ctattttgta ccattatcgc atgctaatct ttgatgtttg    540

atggaaaaga gccacttact tgtatcccct attcgcctga tggcgataca gacgaaaagg    600

ccaaatcgaa gtacagcagg cgctgcacga caagattcct cgaggctcct gatgctcagc    660
```

aacagcaaat taaatgtcgt catagcatct acagtaatta aattgtgtgg catacaaaag 720
aaaacatgta ctagcatgca tgacaggata tcggggcaga aaggtagcat cagctagcgt 780
tggagttgat gcgtaccatg ttgagaaagt gttgcattct tttattcaaa gggggcaaaa 840
tgaatagacg ataggttac 859

<210> SEQ ID NO 15
<211> LENGTH: 633
<212> TYPE: DNA
<213> ORGANISM: Zea mays
<220> FEATURE:
<221> NAME/KEY: misc_feature
<222> LOCATION: (594)..(594)
<223> OTHER INFORMATION: n is a, c, g, or t

<400> SEQUENCE: 15
gtcccccaga tttgctagga caccaccgta cccacacccc ggatcagtta atatcgtaga 60
cataatggcc ctccctgcca tcttccacag ctttcttgaa ctgcatcatg catgcagcag 120
gctgtgctgt ggacctgatc gagtttcaat tgatccaagc aagcaagagg gcagttcaat 180
aaagctgtgg gaaattgcag agagagacca gtcgttgatc ggtcggagat ctccccgaat 240
cgatctcgat cggccggaat tttgggggcc ggccgggagg tggatgatgg ggggtgatta 300
ccatctaggc ggcgccgtgt tggatgatgt accaacatat cactataggc tactttggga 360
acctcagatc cccttcggga ttggaggaaa ttgagatgga aatgaactaa tttcttctct 420 aaccccccttc aatcacgaag gggattcgag tttccaaact agccctatat atatcagagc 480
tagggaggga tattgctgca acatgcatca cgaggtacag atatataatt agggttctgc 540
tgcaatgttt tgactataga tcgttagtga tctgctgtaa ttaataataa tggngatctc 600
gaagcaattc taaacatcat agtagcaggc cca 633

<210> SEQ ID NO 16
<211> LENGTH: 21
<212> TYPE: DNA
<213> ORGANISM: Artificial
<220> FEATURE:
<223> OTHER INFORMATION: PDS miRNA

<400> SEQUENCE: 16
tcagcagcaa tttcaccagg a 21

<210> SEQ ID NO 17
<211> LENGTH: 21
<212> TYPE: DNA
<213> ORGANISM: Artificial
<220> FEATURE:
<223> OTHER INFORMATION: 159c-PDS-star sequence

<400> SEQUENCE: 17
tccaggtgaa tttggtgctg t 21

<210> SEQ ID NO 18
<211> LENGTH: 20
<212> TYPE: DNA
<213> ORGANISM: Artificial
<220> FEATURE:
<223> OTHER INFORMATION: 164h-PDS-star sequence

<400> SEQUENCE: 18
tctggtgaaa acgctgctga 20

<210> SEQ ID NO 19

<211> LENGTH: 21
<212> TYPE: DNA
<213> ORGANISM: Artificial
<220> FEATURE:
<223> OTHER INFORMATION: 168a-PDS-star sequence

<400> SEQUENCE: 19
ccctggcaaa attgctgctg a 21

<210> SEQ ID NO 20
<211> LENGTH: 22
<212> TYPE: DNA
<213> ORGANISM: Artificial
<220> FEATURE:
<223> OTHER INFORMATION: 169r-PDS-star sequence

<400> SEQUENCE: 20
gcctggtgaa cattgctgct ga 22

<210> SEQ ID NO 21
<211> LENGTH: 21
<212> TYPE: DNA
<213> ORGANISM: Artificial
<220> FEATURE:
<223> OTHER INFORMATION: SID21 396h-PDS-star

<400> SEQUENCE: 21
tcctggtgca attgctgctg a 21

<210> SEQ ID NO 22
<211> LENGTH: 684
<212> TYPE: DNA
<213> ORGANISM: Artificial
<220> FEATURE:
<223> OTHER INFORMATION: 159c-PDS miRNA precursor

<400> SEQUENCE: 22
cttttcatag cacctctata cctcttcttc tcgtcgtcac tctatcccgc atctgctgtt 60
ctttatttct atacatacat atatactatc atcggttatt tgcttctcta ttctgtccga 120
gtactttacg gtgttccgca catagatctc gtggccggct gttttgcgct ttcgcttgcg 180
tttcttggcc ctgctggtgt tgaccggtcc gaacgggggc agatcgatgc tttgggtttg 240
aagtccaggt gaatttggtg ctgtgaaggg tcgttccgaa gggctggttc cgctgctcgt 300
tcatggttcc cactatccta tctcatcatg tgtatatatg taatccatgg gggagggttt 360
ctctcgtctt tgagataggc ttgtggtttg catgaccgag gagctgcacc gcccccttgc 420
tggccgctct cagcagcaat ttcaccagga catcctgatc cacccctcca tttttttttg 480
cttgttgcgt ccttcctggg acctgagatc cgaggctcgt ggtggctcac tgtagcctcg 540
ctacactgtt ttcttctcct ctcctgtgct atttgctgtt tctcctaaga ttctttaggc 600
cgtgcttatc cgtgctggag tttaacgaag cagcacgttg ctgctgctgg tgctgccctc 660
atgccctggt ggtcgactgg tatc 684

<210> SEQ ID NO 23
<211> LENGTH: 739
<212> TYPE: DNA
<213> ORGANISM: Artificial
<220> FEATURE:
<223> OTHER INFORMATION: 164h-PDS miRNA precursor

<400> SEQUENCE: 23
ctccttttct ggcacttgag agatgtgtgt gtggtagacg gtggctgtgc gtggtcagca 60

-continued

```
gcaatttcac caggattacc atccaatgcc gccgggtggg tgggtggaat ggatggatgg    120

ttctctggtg aaaacgctgc tgaccgagca cgaactgtct tggatccgcg cgcgcgtgcc    180

gtacatacct cgtcatgcag gagttcaggt gctgcctaat cctcggcggc cctcaccgcg    240

ccaccggcgt ctcgcgtcgt cgctgccgat cgatcgatcg tccagcccgc cgccagttga    300

gttccgaacc ccgatgctta tagcctccca tccctggtta gcaagcatcg tgtgtatctt    360

gcatctcaga cttgcttcct cttcatcatt cattcattca tactcaagca ttaattattc    420

aggaccaagc aagcggtaga attcaaattc aattcgcaca accctttgct tgtcagctag    480

cttaccttgt gtattggatt tgaatacatg ctggtaatcc atctaataag aaagcgctgt    540

gtggcgctac ctgtccgtag tatggccgcg ccgactgtct gtcggctggc atggcatgat    600

atacattcta gttatcttga accaaaggcg actgtccgta gagttgcttg ctcttgcttc    660

agcaggtggg aatggcgccg tgcacttggg ttcgcctgtc tcagttacca gaggagccta    720

atcccatcgt ccctcgtac                                                 739
```

```
<210> SEQ ID NO 24
<211> LENGTH: 791
<212> TYPE: DNA
<213> ORGANISM: Artificial
<220> FEATURE:
<223> OTHER INFORMATION: 168a-PDS miRNA precursor

<400> SEQUENCE: 24

ggttcgcgcg gagggaagga gggagaagaa gcgaagccgc gccgcctcgg gctcagcagc     60

aatttcacca ggaccgccgc ccggccgacg ggacggccct ggcaaaattg ctgctgaatc    120

ggagccggcg gagcgataca gcggccggcc gaccgccgcc tgcttgcctg cgcgcgctgc    180

tctcgactgc ggatgccgcc ctcggtttgt ttgtttgttt ttttctttct gataaggatc    240

gtgctgattg ctgtgactcc gtgtcgccgc ccgtgggaat tgttattagg cgccgtgggg    300

atctctgctc taggttagag taagcagtcc ggatctggat ctggcgcggg tccaaatttc    360

taacctctgg tgagacatct ccgtttttgt ggtgcggggt gcaaaatttg ccggtcatga    420

tgccactcgg atggatcacg gggaaaccat gcctaggtgg attattggtt cggcttcttt    480

taccgctagc ctaccacggg ctcacattgg ttgtaggttt tgtcttagat ttggctcgcc    540

caactgtagg acgaccgttg attggtctac ttgtgtaggt agattgcttg gtagagggga    600

ctcctttttt tctctcaaga aactacgccg gacttcccct gttacatgcg gcctcctgtg    660

tatgtgaggt gatgcgagtg gagtccttga tgaacactag aggctagaaa tccagtgatt    720

aggtgtccag gaatatatgc tcgggggatc agtcaagagg aggtggggaa gagatcaagt    780

agccgattgg c                                                         791
```

```
<210> SEQ ID NO 25
<211> LENGTH: 860
<212> TYPE: DNA
<213> ORGANISM: Artificial
<220> FEATURE:
<223> OTHER INFORMATION: 169r-PDS miRNA precursor

<400> SEQUENCE: 25

ccctccacac agagaagcaa agaaaccaca ccacagtcgt aggggaaggg agaggaggga     60

gggtggcttc tgctgggttg ccatgtgcta tgaggtagag aacgggatgt cagcagcaat    120

ttcaccagga ctcctggaac ctggaggcgt ctcagcttgc tgtgctgtgg cttagaactt    180

agtgcctggt gaacattgct gctgacacct agttctcttc ctctcgtgta tggccctcaa    240
```

```
gcaccgtcaa gagatctagg acctgcattc atatatcatc agcccactcc agaggaaacg    300

taagggcaag tatgcatcta acctcaagtt gacatatttc tatttctcct gcaattttgg    360

gtcttccaaa aaaatcagaa atttgagata tatgaatatt attacaaaca tacagggctt    420

gcatacaata caagcccaag ccccatctgg catcatacgt caaatttcat acatgcatct    480

gtcagacaat atatatcctc actattttgt accattatcg catgctaatc tttgatgttt    540

gatggaaaag agccacttac ttgtatcccc tattcgcctg atggcgatac agacgaaaag    600

gccaaatcga agtacagcag gcgctgcacg acaagattcc tcgaggctcc tgatgctcag    660

caacagcaaa ttaaatgtcg tcatagcatc tacagtaatt aaattgtgtg gcatacaaaa    720

gaaaacatgt actagcatgc atgacaggat atcggggcag aaaggtagca tcagctagcg    780

ttggagttga tgcgtaccat gttgagaaag tgttgcattc ttttattcaa agggggcaaa    840

atgaatagac gataggttac                                                860
```

<210> SEQ ID NO 26
<211> LENGTH: 633
<212> TYPE: DNA
<213> ORGANISM: Artificial
<220> FEATURE:
<223> OTHER INFORMATION: 396h-PDS miRNA precursor
<220> FEATURE:
<221> NAME/KEY: misc_feature
<222> LOCATION: (594)..(594)
<223> OTHER INFORMATION: n is a, c, g, or t

<400> SEQUENCE: 26

```
gtcccccaga tttgctagga caccaccgta cccacacccc ggatcagtta atatcgtaga     60

cataatggcc ctccctgcca tctcagcagc aatttcacca ggacatcatg catgcagcag    120

gctgtgctgt ggacctgatc gagtttcaat tgatccaagc aagcaagagg gtcctggtgc    180

aattgctgct gaaattgcag agagagacca gtcgttgatc ggtcggagat ctccccgaat    240

cgatctcgat cggccggaat tttgggggcc ggccgggagg tggatgatgg ggggtgatta    300

ccatctaggc ggcgccgtgt tggatgatgt accaacatat cactataggc tactttggga    360

acctcagatc cccttcggga ttggaggaaa ttgagatgga aatgaactaa tttcttctct    420

aacccccttc aatcacgaag gggattcgag tttccaaact agccctatat atatcagagc    480

tagggaggga tattgctgca acatgcatca cgaggtacag atatataatt agggttctgc    540

tgcaatgttt tgactataga tcgttagtga tctgctgtaa ttaataataa tggngatctc    600

gaagcaattc taaacatcat agtagcaggc cca                                 633
```

<210> SEQ ID NO 27
<211> LENGTH: 96
<212> TYPE: DNA
<213> ORGANISM: Artificial
<220> FEATURE:
<223> OTHER INFORMATION: 169r-PDS-short miRNA precursor

<400> SEQUENCE: 27

```
tcagcagcaa tttcaccagg actcctggaa cctggaggcg tctcagcttg ctgtgctgtg     60

gcttagaact tagtgcctgg tgaacattgc tgctga                               96
```

<210> SEQ ID NO 28
<211> LENGTH: 305
<212> TYPE: DNA
<213> ORGANISM: Artificial
<220> FEATURE:
<223> OTHER INFORMATION: 169r-PDS-medium miRNA precursor

<400> SEQUENCE: 28
ccctccacac agagaagcaa agaaaccaca ccacagtcgt aggggaaggg agaggaggga 60
gggtggcttc tgctgggttg ccatgtgcta tgaggtagag aacgggatgt cagcagcaat 120
ttcaccagga ctcctggaac ctggaggcgt ctcagcttgc tgtgctgtgg cttagaactt 180
agtgcctggt gaacattgct gctgacacct agttctcttc ctctcgtgta tggccctcaa 240
gcaccgtcaa gagatctagg acctgcattc atatatcatc agcccactcc agaggaaacg 300
taagg 305

<210> SEQ ID NO 29
<211> LENGTH: 117
<212> TYPE: DNA
<213> ORGANISM: Artificial
<220> FEATURE:
<223> OTHER INFORMATION: 396h-PDS-short miRNA precursor

<400> SEQUENCE: 29
atctcagcag caatttcacc aggacatcat gcatgcagca ggctgtgctg tggacctgat 60
cgagtttcaa ttgatccaag caagcaagag ggtcctggtg caattgctgc tgaaatt 117

<210> SEQ ID NO 30
<211> LENGTH: 292
<212> TYPE: DNA
<213> ORGANISM: Artificial
<220> FEATURE:
<223> OTHER INFORMATION: 396h-PDS-medium miRNA precursor

<400> SEQUENCE: 30
gtcccccaga tttgctagga caccaccgta cccacacccc ggatcagtta atatcgtaga 60
cataatggcc ctccctgcca tctcagcagc aatttcacca ggacatcatg catgcagcag 120
gctgtgctgt ggacctgatc gagtttcaat tgatccaagc aagcaagagg gtcctggtgc 180
aattgctgct gaaattgcag agagagacca gtcgttgatc ggtcggagat ctcccgaat 240 cgatctcgat cggccggaat tttgggggcc ggccgggagg tggatgatgg gg 292

<210> SEQ ID NO 31
<211> LENGTH: 684
<212> TYPE: DNA
<213> ORGANISM: Artificial
<220> FEATURE:
<223> OTHER INFORMATION: 159c-FAD miRNA precursor

<400> SEQUENCE: 31
cttttcatag cacctctata cctcttcttc tcgtcgtcac tctatcccgc atctgctgtt 60
ctttatttct atacatacat atatactatc atcggttatt tgcttctcta ttctgtccga 120
gtactttacg gtgttccgca catagatctc gtggccggct gttttgcgct ttcgcttgcg 180
tttcttggcc ctgctggtgt tgaccggtcc gaacgggggc agatcgatgc tttgggtttg 240
aagcgcacga cctgttgacc acctgaaggg tcgttccgaa gggctggttc cgctgctcgt 300
tcatggttcc cactatccta tctcatcatg tgtatatatg taatccatgg gggagggttt 360
ctctcgtctt tgagataggc ttgtggtttg catgaccgag gagctgcacc gccccccttgc 420 tggccgctct ggtggacaag aggtcgtgcg catcctgatc cacccctcca tttttttttg 480
cttgttgcgt ccttcctggg acctgagatc cgaggctcgt ggtggctcac tgtagcctcg 540
ctacactgtt ttcttctcct ctcctgtgct atttgctgtt tctcctaaga ttctttaggc 600
cgtgcttatc cgtgctggag tttaacgaag cagcacgttg ctgctgctgg tgctgccctc 660
atgccctggt ggtcgactgg tatc 684

<210> SEQ ID NO 32
<211> LENGTH: 790
<212> TYPE: DNA
<213> ORGANISM: Artificial
<220> FEATURE:
<223> OTHER INFORMATION: 168a-FAD miRNA precursor

<400> SEQUENCE: 32
ggttcgcgcg gagggaagga gggagaagaa gcgaagccgc gccgcctcgg gctggtggag 60
aagaggtcgt gcgccgccgc ccggccgacg ggacggcgca cgatgtcttc tccaccaatc 120
ggagccggcg gagcgataca gcggccggcc gaccgccgcc tgcttgcctg cgcgcgctgc 180
tctcgactgc ggatgccgcc ctcggtttgt ttgtttgttt ttttctttct gataaggatc 240
gtgctgattg ctgtgactcc gtgtcgccgc ccgtgggaat tgttattagg cgccgtgggg 300
atctctgctc taggttagag taagcagtcc ggatctggat ctggcgcggg tccaaatttc 360
taacctctgg tgagacatct ccgtttttgt ggtgcggggt gcaaaatttg ccggtcatga 420
tgccactcgg atggatcacg gggaaaccat gcctaggtgg attattggtt cggcttcttt 480
taccgctagc ctaccacggg ctcacattgg ttgtaggttt tgtcttagat ttggctcgcc 540
caactgtagg acgaccgttg attggtctac ttgtgtaggt agattgcttg gtagagggga 600
ctcctttttt tctctcaaga aactacgccg gacttcccct gttacatgcg gcctcctgtg 660
tatgtgaggt gatgcgagtg gagtccttga tgaacactag aggctagaaa tccagtgatt 720
aggtgtccag gaatatatgc tcgggggatc agtcaagagg aggtggggaa gagatcaagt 780
agccgattgg 790

<210> SEQ ID NO 33
<211> LENGTH: 861
<212> TYPE: DNA
<213> ORGANISM: Artificial
<220> FEATURE:
<223> OTHER INFORMATION: 169r-FAD miRNA precursor

<400> SEQUENCE: 33
ccctccacac agagaagcaa agaaaccaca ccacagtcgt aggggaaggg agaggaggga 60
gggtggcttc tgctgggttg ccatgtgcta tgaggtagag aacgggatgt ggtggagaag 120
aggtcgtgcg ctcctggaac ctggaggcgt ctcagcttgc tgtgctgtgg cttagaactt 180
agtcgcacga ccttcttctc caccaacacc tagttcttct cctctcgtgt atggccctca 240
agcaccgtca agagatctag gacctgcatt catatatcat cagcccactc cagaggaaac 300
gtaagggcaa gtatgcatct aacctcaagt tgacatattt ctatttctcc tgcaattttg 360
ggtcttccaa aaaaatcaga aatttgagat atatgaatat tattacaaac atacagggct 420
tgcatacaat acaagcccaa gccccatctg gcatcatacg tcaaatttca tacatgcatc 480
tgtcagacaa tatatatcct cactattttg taccattatc gcatgctaat ctttgatgtt 540
tgatggaaaa gagccactta cttgtatccc ctattcgcct gatggcgata cagacgaaaa 600
ggccaaatcg aagtacagca ggcgctgcac gacaagattc ctcgaggctc ctgatgctca 660
gcaacagcaa attaaatgtc gtcatagcat ctacagtaat taaattgtgt ggcatacaaa 720
agaaaacatg tactagcatg catgacagga tatcggggca gaaaggtagc atcagctagc 780
gttggagttg atgcgtacca tgttgagaaa gtgttgcatt cttttattca aagggggcaa 840
aatgaataga cgataggtta c 861

<210> SEQ ID NO 34
<211> LENGTH: 633
<212> TYPE: DNA
<213> ORGANISM: Artificial
<220> FEATURE:
<223> OTHER INFORMATION: 396h-FAD miRNA precursor
<220> FEATURE:
<221> NAME/KEY: misc_feature
<222> LOCATION: (594)..(594)
<223> OTHER INFORMATION: n is a, c, g, or t

<400> SEQUENCE: 34
gtcccccaga tttgctagga caccaccgta cccacacccc ggatcagtta atatcgtaga 60
cataatggcc ctccctgcca tctggtggag aagaggtcgt gcgcatcatg catgcagcag 120
gctgtgctgt ggacctgatc gagtttcaat tgatccaagc aagcaagagg gcgcacgact 180
tcttctccac caaattgcag agagagacca gtcgttgatc ggtcggagat ctccccgaat 240
cgatctcgat cggccggaat tttgggggcc ggccgggagg tggatgatgg ggggtgatta 300
ccatctaggc ggcgccgtgt tggatgatgt accaacatat cactataggc tactttggga 360
acctcagatc cccttcggga ttggaggaaa ttgagatgga aatgaactaa tttcttctct 420
aacccccttc aatcacgaag gggattcgag tttccaaact agccctatat atatcagagc 480
tagggaggga tattgctgca acatgcatca cgaggtacag atatataatt agggttctgc 540
tgcaatgttt tgactataga tcgttagtga tctgctgtaa ttaataataa tggngatctc 600
gaagcaattc taaacatcat agtagcaggc cca 633

<210> SEQ ID NO 35
<211> LENGTH: 21
<212> TYPE: DNA
<213> ORGANISM: Artificial
<220> FEATURE:
<223> OTHER INFORMATION: lethal leaf spot miRNA

<400> SEQUENCE: 35
tttgaaagga cggtgtaagg c 21

<210> SEQ ID NO 36
<211> LENGTH: 21
<212> TYPE: DNA
<213> ORGANISM: Artificial
<220> FEATURE:
<223> OTHER INFORMATION: 168a-lls-star sequence

<400> SEQUENCE: 36
accttaatcc gtcctttcaa a 21

<210> SEQ ID NO 37
<211> LENGTH: 22
<212> TYPE: DNA
<213> ORGANISM: Artificial
<220> FEATURE:
<223> OTHER INFORMATION: 69r-lls-star sequence

<400> SEQUENCE: 37
cccttacacc tgtcctttca ac 22

<210> SEQ ID NO 38
<211> LENGTH: 21
<212> TYPE: DNA
<213> ORGANISM: Artificial
<220> FEATURE:
<223> OTHER INFORMATION: 396h-lls-star sequence

<400> SEQUENCE: 38
gccttacagc gtcctttcaa a 21

<210> SEQ ID NO 39
<211> LENGTH: 21
<212> TYPE: DNA
<213> ORGANISM: Artificial
<220> FEATURE:
<223> OTHER INFORMATION: MRP miRNA sequence

<400> SEQUENCE: 39
taattcacaa tctcaccact c 21

<210> SEQ ID NO 40
<211> LENGTH: 21
<212> TYPE: DNA
<213> ORGANISM: Artificial
<220> FEATURE:
<223> OTHER INFORMATION: 168a-MRP-star sequence

<400> SEQUENCE: 40
aagtggctag attgtgaatt a 21

<210> SEQ ID NO 41
<211> LENGTH: 21
<212> TYPE: DNA
<213> ORGANISM: Artificial
<220> FEATURE:
<223> OTHER INFORMATION: 396h-MRP-star sequence

<400> SEQUENCE: 41
gagtggtgac attgtgaatt a 21

<210> SEQ ID NO 42
<211> LENGTH: 791
<212> TYPE: DNA
<213> ORGANISM: Artificial
<220> FEATURE:
<223> OTHER INFORMATION: 168a-MRP

<400> SEQUENCE: 42
ggttcgcgcg gagggaagga gggagaagaa gcgaagccgc gccgcctcgg gctaattcac 60
aatctcacca ctcccgccgc ccggccgacg ggacggaagt ggctagattg tgaattaatc 120
ggagccggcg gagcgataca gcggccggcc gaccgccgcc tgcttgcctg cgcgcgctgc 180
tctcgactgc ggatgccgcc ctcggtttgt ttgtttgttt ttttctttct gataaggatc 240
gtgctgattg ctgtgactcc gtgtcgccgc ccgtgggaat tgttattagg cgccgtgggg 300
atctctgctc taggttagag taagcagtcc ggatctggat ctggcgcggg tccaaatttc 360
taacctctgg tgagacatct ccgtttttgt ggtgcggggt gcaaaatttg ccggtcatga 420
tgccactcgg atggatcacg gggaaaccat gcctaggtgg attattggtt cggcttcttt 480
taccgctagc ctaccacggg ctcacattgg ttgtaggttt tgtcttagat ttggctcgcc 540
caactgtagg acgaccgttg attggtctac ttgtgtaggt agattgcttg gtagagggga 600
ctcctttttt tctctcaaga aactacgccg gacttcccct gttacatgcg gcctcctgtg 660
tatgtgaggt gatgcgagtg gagtccttga tgaacactag aggctagaaa tccagtgatt 720
aggtgtccag gaatatatgc tcgggggatc agtcaagagg aggtggggaa gagatcaagt 780
agccgattgg c 791

<210> SEQ ID NO 43

-continued

```
<211> LENGTH: 633
<212> TYPE: DNA
<213> ORGANISM: Artificial
<220> FEATURE:
<223> OTHER INFORMATION: 396h-MRP
<220> FEATURE:
<221> NAME/KEY: misc_feature
<222> LOCATION: (594)..(594)
<223> OTHER INFORMATION: n is a, c, g, or t

<400> SEQUENCE: 43

gtcccccaga tttgctagga caccaccgta cccacacccc ggatcagtta atatcgtaga     60

cataatggcc ctccctgcca tctaattcac aatctcacca ctccatcatg catgcagcag    120

gctgtgctgt ggacctgatc gagtttcaat tgatccaagc aagcaagagg ggagtggtga    180

cattgtgaat taaattgcag agagagacca gtcgttgatc ggtcggagat ctccccgaat    240

cgatctcgat cggccggaat tttgggggcc ggccgggagg tggatgatgg ggggtgatta    300

ccatctaggc ggcgccgtgt tggatgatgt accaacatat cactataggc tactttggga    360

acctcagatc cccttcggga ttggaggaaa ttgagatgga aatgaactaa tttcttctct    420

aacccccttc aatcacgaag ggattcgag tttccaaact agccctatat atatcagagc    480

tagggaggga tattgctgca acatgcatca cgaggtacag atatataatt agggttctgc    540

tgcaatgttt tgactataga tcgttagtga tctgctgtaa ttaataataa tggngatctc    600

gaagcaattc taaacatcat agtagcaggc cca                                 633
```